United States Patent
Lussi et al.

(10) Patent No.: US 9,149,347 B2
(45) Date of Patent: Oct. 6, 2015

(54) ABUTMENT FOR A DENTAL IMPLANT

(75) Inventors: Jost Lussi, Basel (CH); Marc Zettler, Basel (CH)

(73) Assignee: Straumann Holding AG, Basel (CH)

( * ) Notice: Subject to any disclaimer, the term of this patent is extended or adjusted under 35 U.S.C. 154(b) by 120 days.

(21) Appl. No.: 13/387,049

(22) PCT Filed: Jul. 27, 2010

(86) PCT No.: PCT/EP2010/004584
§ 371 (c)(1),
(2), (4) Date: Mar. 15, 2012

(87) PCT Pub. No.: WO2011/012285
PCT Pub. Date: Feb. 3, 2011

(65) Prior Publication Data
US 2012/0164602 A1 Jun. 28, 2012

(30) Foreign Application Priority Data
Jul. 27, 2009 (EP) .................................... 09009675

(51) Int. Cl.
*A61C 8/00* (2006.01)

(52) U.S. Cl.
CPC .............. *A61C 8/005* (2013.01); *A61C 8/0089* (2013.01)

(58) Field of Classification Search
CPC .... A61C 8/0048; A61C 8/005; A61C 8/0051; A61C 8/0053; A61C 8/0054; A61C 8/0056; A61C 8/0069
USPC .................. 433/172–176, 177–183; D24/156
See application file for complete search history.

(56) References Cited

U.S. PATENT DOCUMENTS

| 5,779,480 | A | 7/1998 | Groll et al. |
| 5,782,918 | A * | 7/1998 | Klardie et al. ................. 606/60 |
| 5,934,906 | A | 8/1999 | Phimmasone |
| 6,068,479 | A | 5/2000 | Kwan |
| 7,104,797 | B2 * | 9/2006 | Rassoli ......................... 433/173 |
| 7,207,800 | B1 | 4/2007 | Kwan |
| 7,291,012 | B2 * | 11/2007 | Lyren ............................ 433/173 |
| 7,338,286 | B2 | 3/2008 | Porter et al. |
| 2003/0082498 | A1 * | 5/2003 | Halldin et al. ................ 433/173 |
| 2003/0143514 | A1 | 7/2003 | Peltier |
| 2005/0106534 | A1 * | 5/2005 | Gahlert ......................... 433/173 |
| 2006/0078847 | A1 | 4/2006 | Kwan |
| 2007/0037123 | A1 * | 2/2007 | Mansueto et al. ............ 433/173 |
| 2007/0202462 | A1 * | 8/2007 | Schwarz et al. .............. 433/172 |

(Continued)

FOREIGN PATENT DOCUMENTS

| EP | 1 269 932 A1 | 1/2003 |
| WO | WO 02/45615 A1 | 6/2002 |

(Continued)

OTHER PUBLICATIONS

Dec. 2, 2010 International Search Report and Written Opinion in PCT/US2010/004584.

*Primary Examiner* — Yogesh Patel
(74) *Attorney, Agent, or Firm* — Novak Druce Connolly Bove + Quigg LLP

(57) ABSTRACT

An abutment (10) for supporting a dental prosthesis including a post (30) and a shoulder (10a), wherein the shoulder comprises a concavely curved chamfer surface extending radially outwards from a base of the post, the post comprising at least one flat surface (35) which runs directly into the chamfered surface such that the chamfered surface is non-uniform.

12 Claims, 11 Drawing Sheets

(56) References Cited

U.S. PATENT DOCUMENTS

| | | | |
|---|---|---|---|
| 2010/0119995 A1* | 5/2010 | Grant et al. | 433/174 |
| 2011/0143315 A1 | 6/2011 | Guenter et al. | |

FOREIGN PATENT DOCUMENTS

| | | |
|---|---|---|
| WO | WO 03/037208 A1 | 5/2003 |
| WO | WO 2006/035011 A1 | 4/2006 |
| WO | WO 2006/138353 A2 | 12/2006 |
| WO | WO 2007/039206 A1 | 4/2007 |
| WO | WO 2008/138644 A1 | 11/2008 |
| WO | WO 2008138644 A1 * | 11/2008 |
| WO | WO 2009/060415 A2 | 5/2009 |
| WO | WO 2010/025839 A1 | 3/2010 |

* cited by examiner

ABUTMENT FOR A DENTAL IMPLANT

FIELD OF THE INVENTION

The present invention relates to an abutment for a dental implant made of a ceramic material or other material.

BACKGROUND

Implants have long been used in the field of implant dentistry. Dental implants are used to replace individual teeth or as a support structure for anchoring more complex abutment structures, which generally replace several or even all of the teeth. The materials used for the dental implants are often titanium and alloys thereof, and increasingly ceramic materials. These materials have the necessary strength for withstanding the mechanical loads that occur, and they are at the same time sufficiently biocompatible.

The shape and construction of the dental implant depends mainly on the exact purpose for which it is used. The implants are often constructed in two parts, in which case they consist of an anchoring part, often referred to in isolation as the implant, and of a separate abutment. The anchoring part is either embedded completely in the bone, that is to say to the height of the alveolar crest, or protrudes by a few millimeters from the alveolar crest into the soft tissue. The abutment is mounted on the anchoring part either after the latter has become incorporated (osseointegrated) into the bone or directly after the anchoring part has been inserted. It can also be attached to the anchoring part prior to insertion. Ultimately, the desired prosthetic element (e.g. bridge or crown) is connected to the abutment. The prosthetic element can be adhesively bonded, cemented or screwed onto the abutment. It is also possible for the implant to be constructed in one part, such that the anchoring part and the abutment are produced from one piece. Hence in such implant systems the integral anchoring part and abutment are positioned within the mouth at the same time.

One-part implants have good mechanical stability but have disadvantages from an aesthetic point of view. Such implants are currently made in most cases of titanium or a titanium alloy, which is why the visible part of the implant can create an undesired metallic appearance. In addition the abutment shape and angulation, relative to the anchoring part, must be selected prior to insertion. This provides the surgeon with less flexibility and room for error in the placement of the implant.

By contrast, two-part implants are more versatile in use, because the anchoring part and the abutment can be adapted individually to the particular requirements. However, the multi-part structure can have a negative impact on the mechanical stability of the overall implant or the overall structure. An advantage of two-part implants is that the abutment can be made from a different material than the anchoring part, and in this way a surface can be obtained whose colour merges satisfactorily with the surrounding tissue.

In recent times, ceramic materials with sufficient mechanical stability have also become available, such that one-part or two-part dental implants can be produced from ceramic materials.

EP 1 609 436 describes a ceramic implant of this kind. The dental implant is composed of an anchoring part for anchoring in the bone and of an abutment for receiving a prosthetic superstructure. The implant is produced in one piece from a material based on zirconium oxide.

The dental implants known from the prior art and made of a ceramic material or other material have proven difficult to handle. The abutment often has a more or less circular cylindrical shape which, combined with the hard and smooth surface of the ceramic material, makes it difficult to grip. In addition, the abutment section of a one piece implant has to have special structures, e.g. grooves, indents, projections and the like, in order to allow the dental implant to be screwed into the drilled hole provided for it. In conventional abutments, there is also a danger that the prosthetic elements mounted on them will break relatively easily in their apical end area. This is because of the shaping which, in the apical end area of the prosthetic elements, must narrow in diameter and smoothly join to the circumference of the implant. In the end area of the prosthetic element lying on the abutment therefore, fractures may occur in thin-walled areas under mechanical loading. This is a particular problem with ceramic prosthetics, which are brittle and therefore prone to chipping.

SUMMARY OF THE INVENTION

The object of the present invention is therefore to make available an abutment for a dental implant, which abutment is easy to handle, in particular easy to grip, and provides a very good support and shape for clinically advantageous prosthetic elements of high stability that are to be mounted thereon, in particular ceramic prosthetic elements.

An abutment according to the present invention has substantially the shape of a truncated cone, said abutment having a shoulder. The truncated cone forms an outer surface comprising an at least partially flat surface, wherein the at least partially flat surface runs out into the shoulder.

An abutment according to the present invention provides excellent handling. The at least partially flat surface of the abutment greatly improves the grip of the dental implant in particular, as a result of which the danger of the implant slipping and/or being dropped is greatly reduced. Moreover, a one piece dental implant with an abutment according to the invention is much easier to screw in, since a torque can easily be transmitted to the dental implant in an optimal manner via the at least partially flat surface of the abutment. Complicated shapes on the abutment, e.g. grooves, indents and the like, are no longer necessary. A similar advantage exists in situations in which the abutment forms part of a two part implant and is screwed into the anchoring part. Once again torque can be transmitted via the at least partially flat surface(s) and without the need for complicated shapes.

The shoulder comprises a concavely curved chamfer surface into which the at least partially flat surface runs. The shoulder extends about the entire circumference of the abutment and serves as a support surface for the apical end area of the prosthetic element when this is placed on the abutment. The shoulder can be formed entirely of this chamfered surface or the shoulder may further comprise a planar platform, in which case the chamfered surface extends from the cone to the platform, thus forming a smooth transition between the outer surface of the cone and the planar platform.

Providing a concavely curved shoulder is known from prior art abutments. A curved shoulder is beneficial from both a manufacturing and force distribution perspective. However, in prior art abutments the chamfer is uniform, i.e the surface is formed by a radius rotated 360° about the longitudinal axis of the abutment to form a smooth, continuous surface having no angles. In other words, the base of the abutment post from which the chamfer extends is circular or elliptical in shape. This is the case even when the abutment post comprises one or more flat surfaces, as the flat surface finishes above the chamfer, thus enabling the chamfer to start from a circular or oval outer surface. This necessitates the need for an intermediate or secondary shoulder to join the base of the flat surface to the base of the abutment post and the start of the shoulder. A uniform shoulder chamfer is generally believed to be necessary in order to ensure a good connection between the base of the prosthetic component and the abutment.

The inventors of the present invention however have realised that this uniform shoulder chamfer is not, in fact, essential and that a good connection between the abutment and prosthesis can also be obtained with a non uniform chamfer. This enables the flat surface of the abutment post to "run out" directly into the shoulder. In other words, the curved chamfer of the shoulder begins at the apical end of the flat surface, creating a direct transition between the flat surface and the abutment shoulder without the need for an intermediate shoulder. It has been found that this non-uniform chamfered shoulder does not in fact result in a looser connection between the prosthesis and abutment and in fact this new design has additional benefits.

The absence of complicated shapes, e.g. multiple shoulders makes production very much easier. The fact that the at least partially flat surface runs out directly into the shoulder, without a further (intermediate) shoulder being formed, means that the internal cavity of the prosthetic element is simplified, leading to improved support on the abutment. In addition, as the flat surface does not need to terminate above the shoulder but can run into this, the length of the flat surface is increased and hence a larger gripping and torque transmission surface can be achieved.

The simplified shape of the abutment facilitates the production and application of prosthetics that provide a good fit. By virtue of their simplified shape, the abutments according to the invention can be very easily worked, that is to say they can be easily ground for example. Moreover, this also means that abutments according to the invention have a good, that is to say an advantageous and simple production. A further aspect and advantage is that abutments according to the invention also have very good visibility in imaging methods (e.g. scannability in CAD/CAM). They can be very easily and precisely identified in the images resulting from the imaging methods. This is advantageous especially when several images are superposed, since the precision of the superpositioning is in this way greatly enhanced.

According to one aspect therefore, the present invention provides an abutment for supporting a dental prosthesis comprising a post and a shoulder, wherein the shoulder comprises a concavely curved chamfer surface extending radially outwards from the base of the post, the post comprising at least one flat surface which runs directly into the chamfered surface such that the chamfered surface is non uniform.

By non-uniform it is meant that the chamfer does not form a smooth, continuous surface having no angles, such as when the base of the post is circular or elliptical in shape. Instead the base of the post comprises at least one linear section formed by the at least one flat surface. This results in a discontinuous, or angled, chamfer surface. The angles within the chamfer can be sharp or rounded, i.e. they can occur over a transition radius.

As mentioned above, the shoulder can consist entirely of the chamfered surface. In such embodiments the chamfer runs from the base of the post to the outer perimeter of the abutment shoulder. It is preferable for this perimeter to be substantially circular in shape and hence, when the shoulder consists entirely of a chamfered surface the shoulder perimeter will be uneven in height or the chamfer must comprise different radii of curvature in order to take account of the differing distances from the longitudinal axis at which the chamfer begins. Both of these options present manufacturing problems however.

Preferably therefore, the shoulder further comprises a planar platform. In such embodiments the chamfer depth, i.e. the distance from the base of the post to the outer perimeter of the shoulder, is greater than the radius of curvature of at least part of the chamfered surface. The curved chamfer surface therefore runs out into a planar platform. This platform provides an abutment surface for the prosthesis and thus a strong support. Further it enables the apical end of the prosthesis to be thicker and hence less prone to breakages. The planar platform can also act as a height stop for auxiliary dental devices, as will be explained below. In such embodiments the chamfered surface provides a smooth transition between the base of the post, which includes at least one flat surface, and the platform.

In some embodiments the planar platform is not continuous, i.e. there are some sections of shoulder in which the chamfer extends to the shoulder perimeter. However, preferably chamfer depth is greater than the radius of curvature of the whole of the chamfered surface and thus the planar platform extends around the full circumference of the abutment. Due to the non uniform nature of the chamfer the width of the planar platform is preferably also non uniform. This simplifies the design of the chamfer surface, as this can have a uniform radius of curvature while still allowing the shoulder perimeter to be circular. It also increases the width of the planar platform in those regions of the shoulder which extend from the flat surface. Preferably therefore, the planar platform extends around the full circumference of the abutment and is wider in those regions lying adjacent to the at least one flat surface.

The abutment post is shaped to provide core strength to a dental prosthesis, i.e. it must be shaped and dimensioned such that a dental prosthesis can be placed over the post. Preferably the post is generally cylindrical or frustoconical in shape. In a preferred embodiment the post has the general form of a truncated cone. The tapered nature of the abutment is beneficial when the abutment is used to support a bridge, as the taper enables the bridge to be attached even if there is some divergence between implants. Most preferably, the truncated cone or cylinder has a fully or partially circular geometric base, such that the one or more flat surfaces are interposed between curved surfaces.

Providing a mixture of flat and curved sides increases the volume and surface area of the abutment post compared to posts comprised entirely of flat sides. This increases the strength of the abutment and also provides a larger retention surface for cemented crowns.

In the context of the present invention it should be noted that the base of the post does not necessarily correspond to its geometric base. For example, in geometric terms a cone is defined as a shape that tapers smoothly from a base shape to an apex, i.e. the lateral surface of the cone is formed by straight line segments extending from the apex to the perimeter of the base shape. A truncated cone of course is a cone with the apex cut off by a plane, which in the context of the present invention does not need to be parallel to the base plane. The post base of the present invention however simply refers to the physical base of the post, at which point the lateral surface of the post ends and the chamfered surface begins.

This base can be at right angles to the axis of the post or angled with respect to this.

Although the base of the post does not need to correspond to the geometric base, in some embodiments this is the case. In these embodiments therefore the flat surface forms a part of the lateral surface of the cone or cylinder and extends along the full length of the post. In cases in which the post is tapered, the flat surface will thus extend at an angle to the longitudinal axis.

In a preferred embodiment, the flat surface is arranged parallel to the longitudinal axis of the post. The production of the dental implant is thereby simplified. The flat surface does not need to extend over the full length of the post but should have sufficient length to provide a suitable gripping and force transmission surface. In the direction parallel to the longitudinal axis of the abutment, the length of the at least partially flat surface is preferably at least three millimeters.

As mentioned above, the flat surface can be formed by the geometric base of the post. Alternatively it could be formed by a protrusion in the post surface. However, preferably the flat surface is a bevel surface formed in the post. In other words, the flat surface is formed by a plane intersecting the post. Such a surface is easy to manufacture. In addition, a bevelled surface increases the chamfer depth in the area of the flat surface and thus the surface area of the shoulder in this region is increased. By means of the greater surface area of the shoulder, which serves as a support surface for the end area of the prosthetic element, the apical end area of the prosthetic element can be made thicker, while the shoulder diameter of the abutment remains constant. The risk of breaks occurring in the end area of prosthetic elements is thus greatly reduced. When the same radius (or similar radii) of curvature is used to create the whole of the chamfered surface, a larger area of planar platform is created in the area adjacent to the bevelled surface. This enables a further increase in the width of the apical end of the prosthesis.

The abutment post preferably comprises at least two flat surfaces. This means that when the abutment or one-piece implant is being screwed in, a larger force, that is to say a greater torque, can be applied. The force is also transmitted more uniformly. Locally elevated surface pressures are minimized.

In a preferred embodiment, the flat surfaces are arranged lying opposite each other in pairs.

In an alternative preferred embodiment, the two flat surfaces are not arranged lying opposite each other in pairs, but are arranged at an angle α, preferably of 90°, relative to each another about a longitudinal axis of the abutment. This embodiment has no rotational symmetry with the exception of the identity. This has the advantage that the rotation position of the abutment according to the invention can be more easily displayed.

In another embodiment, the abutment comprises two, particularly preferably four, flat surfaces. In this way, the handling of the implant can be further simplified and the transmission of force during the screwing-in of the implant can be further increased. Preferably four flat surfaces are arranged at 90° relative to each other about a longitudinal axis of the abutment. This forms a rotationally symmetric post and enables a uniform transmission of torque.

In a preferred embodiment, the abutment according to the invention is formed in one piece with an anchoring part. The abutment is therefore integral with the anchoring part. In other words the present invention provides a dental implant comprising an anchoring part for anchoring in the bone and an integral abutment as herein described.

The one-piece design is very favourable in terms of the mechanical load-bearing capacity of the overall system, that is to say of the whole dental implant. Moreover, one-piece dental implants are also preferred from the point of view of manufacturing technology, as there is no requirement for a connecting geometry between the anchoring part and the abutment. One-piece dental implants are also referred to as one-part implants. By contrast, dental implants composed of two separate parts, namely the anchoring part and the abutment, are referred to as two-part.

A one piece dental implant comprising an abutment according to the invention has an anchoring part, for anchoring in the bone, and an abutment. The abutment may have substantially the shape of a truncated cone. The abutment in the shape of a truncated cone forms an outer surface, said outer surface comprising an at least partially flat surface, which runs out directly into the shoulder of the abutment.

The anchoring part preferably has a substantially circular cylindrical shape, although it is possible for the anchoring part to be tapered along its length. In addition, the anchoring part generally has one or more threaded sections and a tip at its apical end.

In another embodiment, the abutment according to the present invention is arranged for use with a separate anchoring part. That is to say, the resulting dental implant is at least in two parts. This permits the combination of different abutments with the same anchoring part or the same abutment with different anchoring parts. The abutment and the anchoring part can also be made of different materials. In such embodiments the abutment further comprises a connection section apical to the shoulder which is configured for connection to a dental implant.

This connection between implant and abutment could be by way of an internal bore within the implant or an external boss protruding from the coronal end of the implant. In each case the connection section of the abutment comprises a complementary co-operating structure, either for insertion into the internal bore or receipt of the implant boss. Preferably the connection section comprises anti-rotation means to prevent relative rotation between the implant and abutment. The implant and abutment can be connected together by means of a screw or other third component, or via bonding, gluing etc. When a connecting screw is used the abutment further comprises a screw passage.

In a preferred embodiment, the abutment is made of a ceramic material. Ceramic materials are particularly preferably chosen from the group of zirconium oxide and aluminium oxide. These ceramic materials have good mechanical stability and give the abutment the required strength. Moreover, a tooth-like colour can be obtained. A very particularly preferred ceramic material is one composed of a stabilized zirconium oxide containing 92.1 to 93.5% by weight of $ZrO_2$, 4.5 to 5.5% by weight of $Y_2O_3$, and 1.8 to 2.2% by weight of $HfO_2$. When produced by sintering with subsequent hot isostatic re-pressing, such a zirconium oxide has a very high mechanical stability.

In another embodiment, the cone angle of the truncated cone is in a range from 1° to 20°. The cone angle is preferably in a range from 4° to 10°. A cone angle of between substantially 6° and substantially 8° is particularly preferred. Cone angle is to be understood as the angle between a surface line and the cone axis at the cone point. The surface line and the cone axis intersect at the cone point. The cone axis is also referred to as the longitudinal axis. In the case of a truncated cone, the cone axis and the surface line are to be continued past the top surface of the truncated cone to the imagined cone point. Twice the cone angle is also referred to as the apex angle. This is the angle between two opposite surface lines which together with the cone axis lie in a sectional plane of the truncated cone.

The present invention also extends to auxiliary dental pieces which are used by the dentist and dental technician during prosthetic planning and creation. For example, healing caps, impression caps and copings are all devices which must fit snugly over the abutment post at different stages of the process.

Healing caps protect the abutment after positioning in the mouth but before the prosthesis has been attached.

Impression caps must accurately transfer the position and orientation of the abutment to a mould of the patient's mouth. This is done by fitting the cap over the abutment and placing a tray (spoon) containing impression material over the patient's teeth and the implant site. Once this material has hardened the tray is removed, with the impression cap remaining in the impression material. An analog of the abutment can then be fixed into the impression cap and the impression material mould is then used to cast a model of the patient's mouth, with the analog providing an exact copy of the abutment.

A coping is placed over the analog and used as a base to create the wax model of the final, or temporary, prosthesis.

All of the above described devices must therefore securely fit over the post of the abutment. In order to achieve this therefore, in accordance with the present invention there is provided an auxiliary dental device for attachment to a dental abutment comprising a cavity, said cavity being complementary in shape to the post of said dental abutment such that said cavity comprises, at its apical end a convexly curved chamfer surface and, coronal to said surface, at least one flat surface that runs directly into said chamfer surface such that said chamfer surface is non uniform.

The auxiliary device is preferably one of a healing cap, impression cap or coping.

Another important auxiliary piece is the insertion device. This instrument transmits torque to the implant or abutment such that this can be screwed into the bone cavity or anchoring part of the implant. This is achieved via the at least one flat surface of the abutment post. As stated above, as the at least one flat surface of the post runs into the shoulder the length of this surface can be increased, providing a larger surface area for torque transmission. In addition, in embodiments in which the shoulder further comprises a planar platform, this creates an abutment surface for the insertion tool, as well as the other auxiliary devices. This planar surface acts as a height stop and informs the user when the insertion tool is correctly seated on the abutment, thus preventing either incomplete alignment of the torque transmission surfaces or excessive force being applied to ensure complete alignment. Such excessive force can damage the abutment or cause jamming of the tool on the abutment.

In relation to small diameter implants, e.g. below 3.5 mm diameter, the increase in planar platform in the region of the at least one flat surface enables a height stop to be formed in situations in which this would not be possible with a uniform chamfer.

Therefore, viewed from a further aspect the present invention comprises an insertion tool for use with a dental abutment having a post comprising at least one flat bevelled surface and a shoulder, the shoulder comprising a concavely curved chamfer surface extending radially outwards from the base of the post to a planar platform, the at least one flat surface running directly into the chamfered surface, the insertion tool comprising a cavity, the inner wall of said cavity comprising at least one flat surface for torque transmission to said abutment, and a distal end, said distal end comprising abutment surfaces at least partially corresponding to the planar platform of the abutment such that in use the abutment surfaces rest on said planar platform. The invention also extends to a combination of the above described abutment and insertion tool.

Preferably the abutment surfaces correspond only to those areas of the platform in the region of the at least one flat surface, i.e. those areas of the platform having an increased width. In other embodiments however the abutment surface fully corresponds to the planar platform.

Viewed from another aspect the present invention provides an auxiliary dental device comprising a post and a shoulder wherein the shoulder comprises a concavely curved chamfer surface extending radially outwards from the base of the post, the post comprising at least one flat surface which runs directly into the chamfered surface such that the chamfered surface is non uniform, the device further comprising, apical to said shoulder, a cylindrical support column.

Preferably the auxiliary device is a try-in piece for use by the surgeon during preparation of the implant site to ensure that the implant will be correctly seated. In this embodiment the cylindrical support comprises a threadless, circular cylindrical column having a diameter and length equal to or less then a dental implant anchoring portion. Preferably the diameter of the column is between 2 and 4 mm and the length is between 8 and 10 mm.

In another preferred embodiment the auxiliary device comprises an analog for transferring the position of an abutment located in a patient's mouth to a model of said mouth. In such embodiments the support column comprises hollows or indents for the inflow of impression material.

BRIEF DESCRIPTION OF THE DRAWINGS

Preferred embodiments of the dental abutment according to the invention will now be described, by way of example only, with reference to the accompanying drawings, in which.

DETAILED DESCRIPTION

Figure 1:
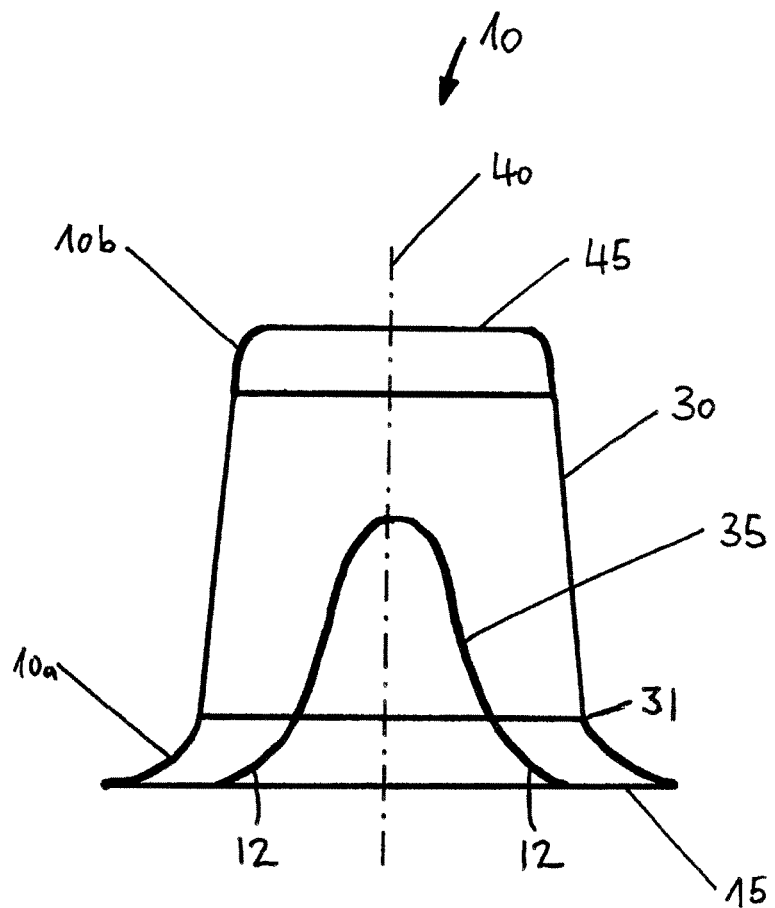
FIG. 1 shows an abutment according to one embodiment of the invention, with a flat surface directed toward the observer.

FIG. 1 shows an abutment 10 according to one embodiment of the present invention. The abutment comprises a truncated conical post 30 and a shoulder 10a. The shoulder comprises a concavely curved chamfer surface which extends from the base 31 of the post 30. The top of the post 30 has rounded edges 10b. The conical post 30 comprises a flat surface 35 which extends to the base 31 of the conical post 30. In this embodiment, flat surface 35 is a bevel surface, as will be discussed in more detail below. The chamfered surface extends from this flat surface 35, thus forming a non-uniform surface having angles 12 at the intersection between the part of the chamfer extending from the flat surface 35 and those parts extending from the conical surface. These angles can be sharp or rounded.

Figure 2:
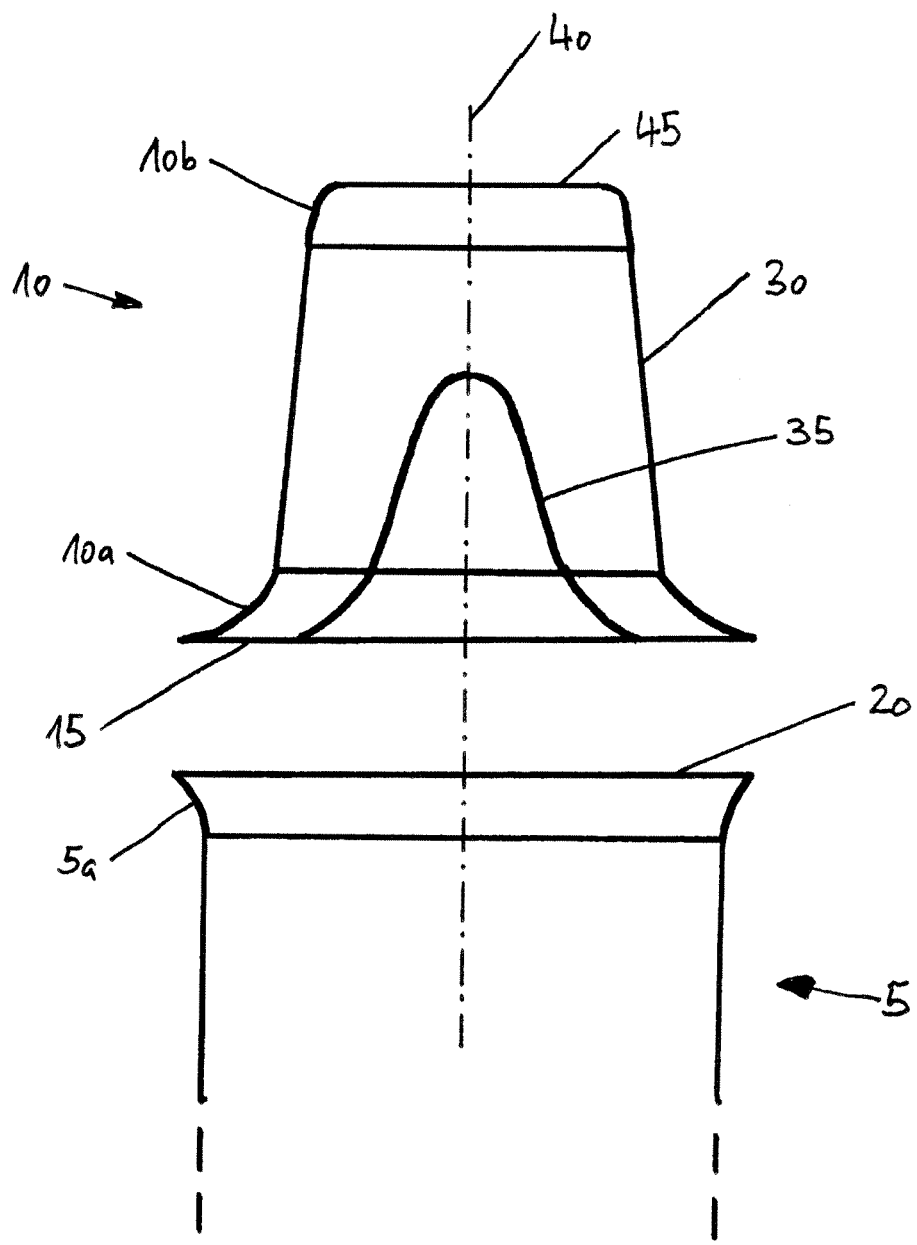
FIG. 2 shows an exploded view of an abutment according to the invention with an anchoring part.

FIG. 1 shows the abutment 10 in isolation. The abutment can either form part of a one piece implant or it can be a separate element arranged for attachment to the anchoring part of a two piece implant. FIG. 2 shows a very schematic representation of the abutment 10 of FIG. 1 as part of a two piece implant. The anchoring part 5, also referred to in isolation as an implant, is shaped for insertion into the jaw bone. To assist with primary stability the anchoring part 5 can comprise threads (not shown). The surface of the anchoring part 5 may also be structured to aid osseointegration. The anchoring part 5 may be intended for complete insertion into the bone, in which case top surface 20 will in use be level with the top surface of the alveolar crest. Such an implant is known as a "bone level" implant. Alternatively the anchoring part 5 may be designed for protrusion into the soft tissue, a so-called "tissue level" implant. In either case, but particularly when the anchoring part forms a tissue level implant, the coronal end of the anchoring part tapers outwards to form a shoulder 5a. This tapered shape helps to form a realistic emergence profile, mimicking the transgingival shape of a natural tooth.

When the anchoring part 5 and abutment 10 are separate components, each must comprise connecting means which enable the elements to be firmly and securely fastened together. These aspects of the abutment 10 and anchoring part 5 are not shown but can comprise one of the many well known methods of attachment. For example, the anchoring part 5 may comprise a blind bore extending from the top surface 20 into the anchoring part and the abutment 10 may comprise a protrusion extending from its lower surface 15 which can be inserted into and fixed within the implant bore by way of a screw or bonding. Alternatively the anchoring part 5 may comprise a boss protruding from the upper surface 20 and the abutment 10 can comprise a corresponding indent in its lower surface 15. The method of connection and the structure of the connecting means do not however form part of the present invention and are therefore not shown or discussed in detail.

The outer perimeter of shoulder 5a matches that of shoulder 10a such that, when the anchoring part 5 and abutment 10 are connected the upper surface 20 of the anchoring part 5 is sealed.

In other embodiments however the shoulder 10a may not sit directly on the anchoring part 5 but may be located coronal to this. In this case the structure of the abutment 10 apical to the shoulder 10a is designed for sealing contact with the anchoring part 5.

Figure 3:
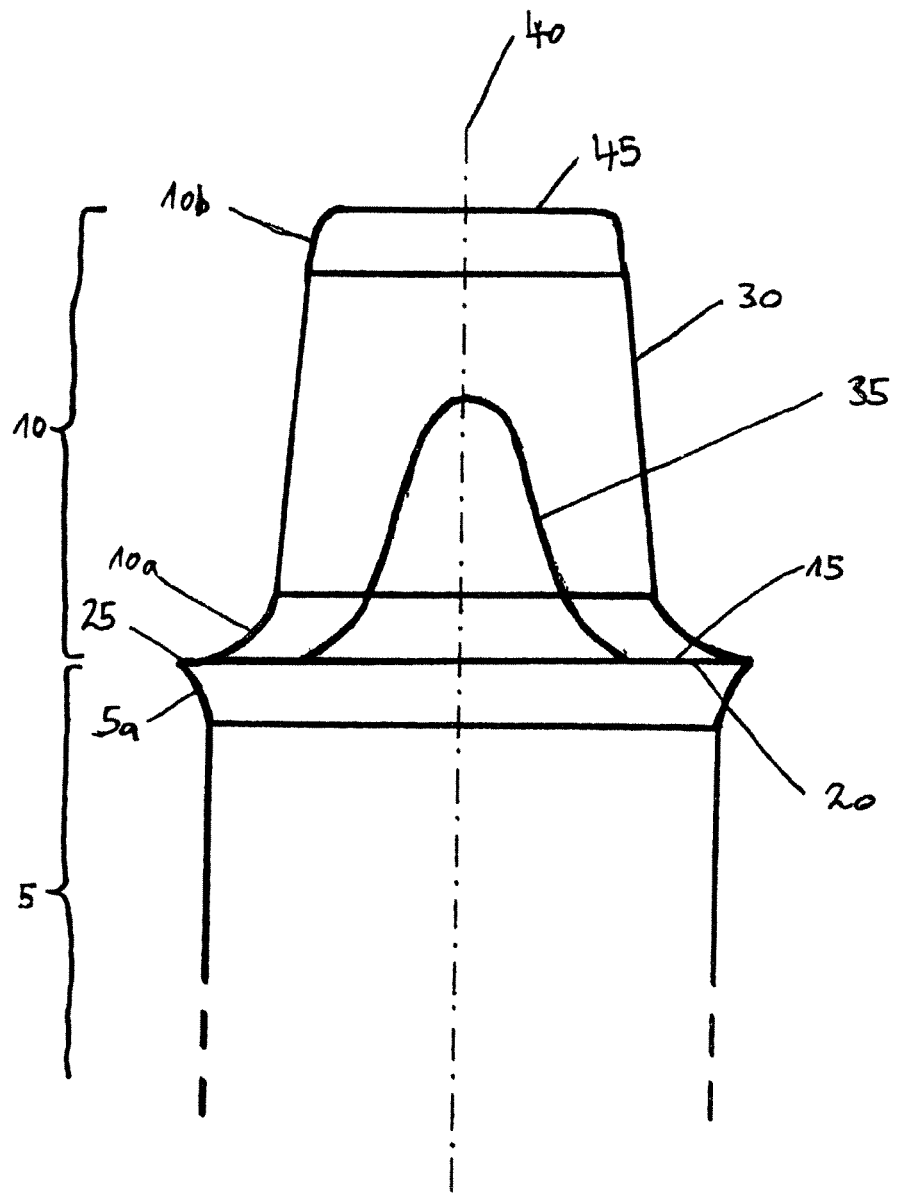
FIG. 3 shows a dental implant with an abutment according to the invention, having a flat surface which is directed toward the observer.

FIG. 3 shows the anchoring part 5 and abutment 10 of FIG. 2 in the connected position. Alternatively this Figure can also be viewed as showing a one piece implant, in which the anchoring part 5 and abutment 10 are formed integrally, from one piece. In both cases the external look of the implant is the same.

Figure 4:
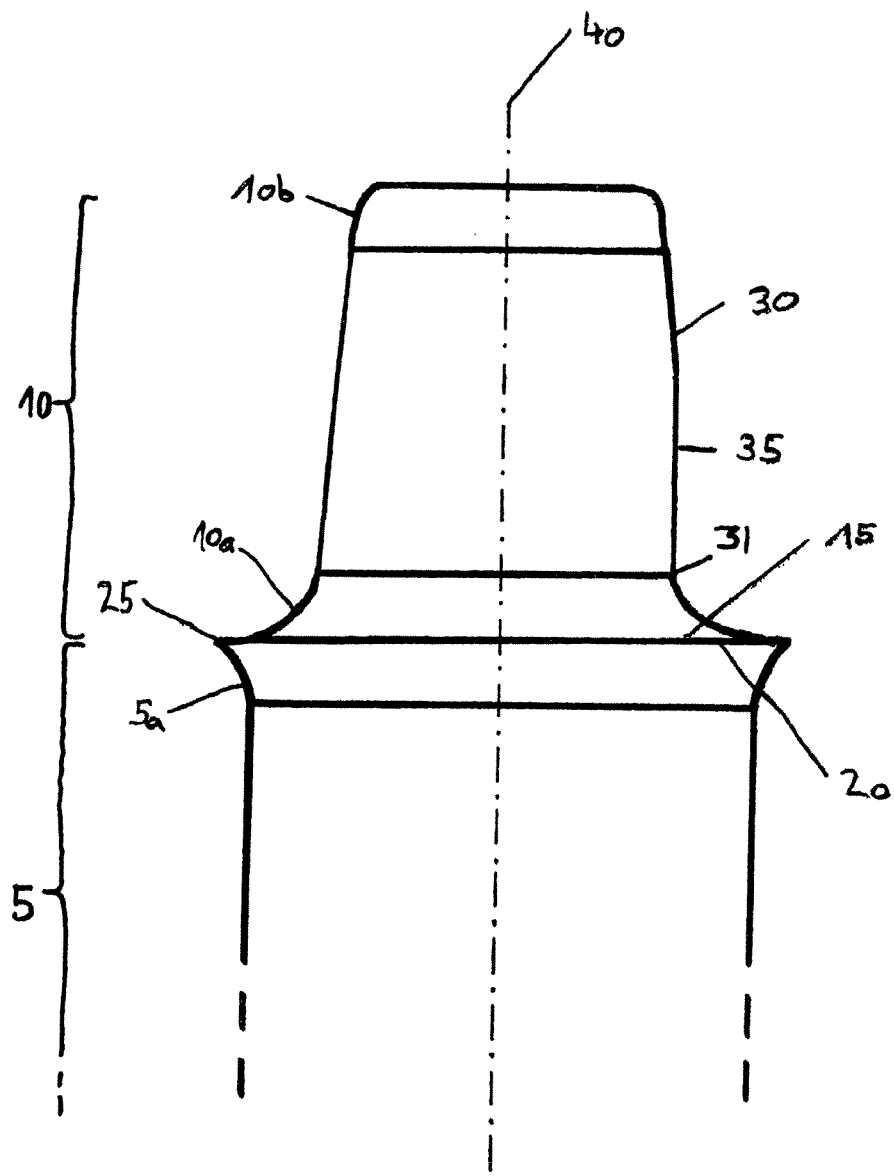
FIG. 4 shows the dental implant from FIG. 3 when said implant is turned through 90° about its longitudinal axis, with the flat surface seen from the side.

In FIGS. 1-3 the flat surface 35 of the abutment 10 is shown facing the observer. FIG. 4 shows the implant of FIG. 3 turned 90° such that the flat surface 35 is shown in profile. In this embodiment the flat surface 35 is a bevel and is parallel to the longitudinal axis 40 of the abutment 10. In this embodiment therefore the flat surface 35 does not extend along the full length of the conical post 30 and furthermore the base 31 of the post 30 does not correspond to its geometric base. The bevelled surface results in a reduction in the volume of the post 30. As can be clearly seen from FIG. 4, the chamfered surface of the shoulder 10a extends directly from the flat surface 35, with no intervening intermediate shoulder. There is therefore a direct transition between the flat surface 35 and the abutment shoulder 10a. This results in a non uniform chamfered surface. In addition, due to the bevelled nature of flat surface 35, the chamfered surface begins closer to the longitudinal axis 40 of the post 30 in those areas which extend from the flat surface 35.

Figure 5:
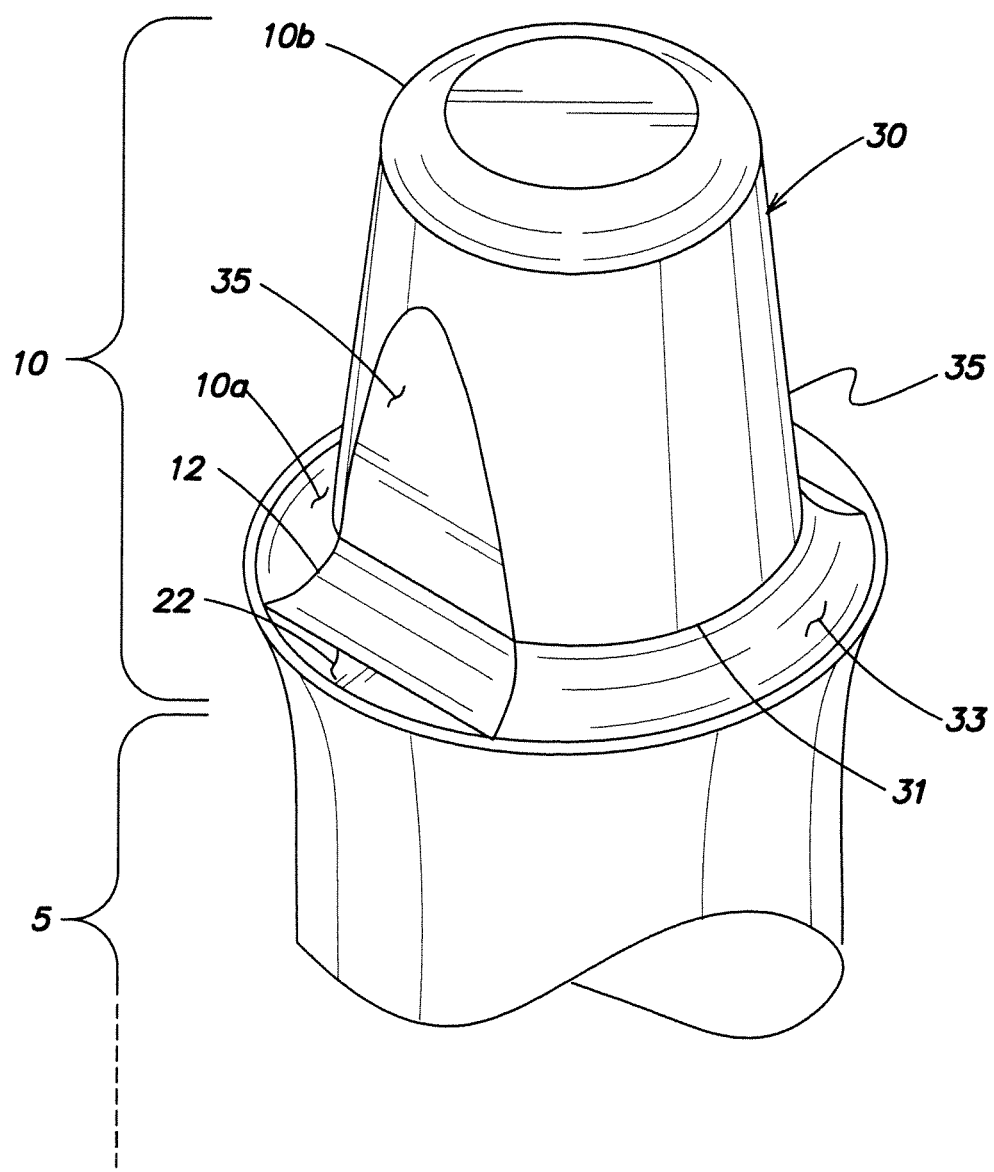
FIG. 5 shows a perspective view of a dental implant with an abutment according to the invention having two flat surfaces.

The non uniform nature of the chamfer can be more clearly seen in FIG. 5. FIG. 5 shows a perspective view of the implant of FIG. 4. In this figure it can be seen that abutment 10 has two opposing flat surfaces 35. These bevelled surfaces extend to the base 31 of the conical post 30. Chamfered surface 33 extends from the base 31 to form a shoulder 10a. As the chamfer depth of the shoulder 10a is greater than the radius of curvature of the chamfer, shoulder 10a also comprises a planar platform 22. The chamfered surface 33 provides a smooth transition from the conical post 30 to this platform 22. As the chamfered surface 33 extends directly from the flat surfaces 35, the chamfered surface 33 is not uniform and instead comprises angles 22. Contrary to previously held opinion, it is not necessary to provide a uniform, non angled chamfered surface at the abutment shoulder 10a. Instead it has been found that a strong connection can be formed between a prosthesis and an abutment 10 when a non-uniform chamfer is used.

In addition, as the flat surfaces 35 are bevelled surfaces and as chamfered surface 33 has an approximately uniform radius of curvature, a greater surface area of planar platform 22 is provided in the vicinity of the flat surfaces 35. A planar platform 22 is beneficial as it provides a firm abutment surface for the prosthesis and an increased support for auxiliary devices, thus forming a height stop. In addition it increases the thickness of the apical end of the prosthesis, as demonstrated in FIGS. 5A and 5B.

Figure 5A:
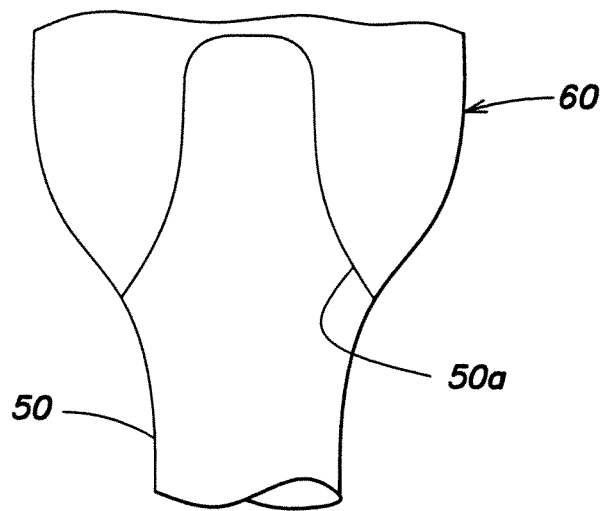
FIG. 5A shows a cross-section through a prosthesis supported on an implant with a curved abutment shoulder.

FIG. 5A shows a partial cross section through a one piece implant 50 having a curved shoulder 50a. As discussed above, the prosthesis 60 must join smoothly to the implant 50 in order to create a realistic emergence profile and to prevent the creation of gaps or an overhang where bacteria could build up. This requires that the apical end of the prosthesis 60 is narrow and hence liable to be damaged, particularly when the prosthesis is formed of a brittle material, such as ceramic.

Figure 5B:
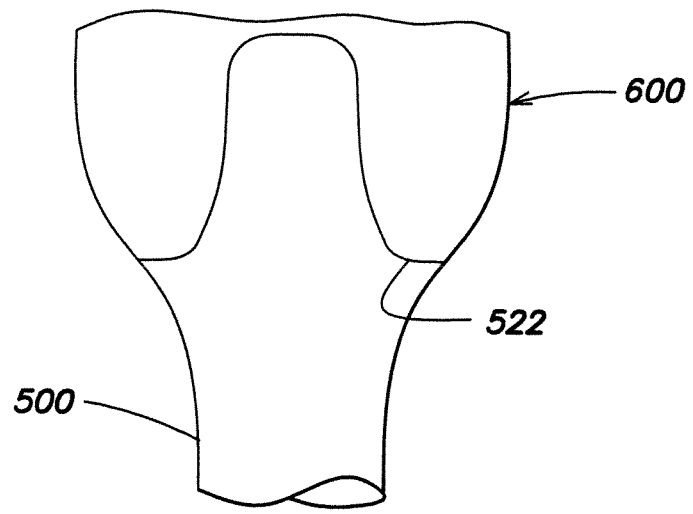
FIG. 5B shows a cross-section through a prosthesis supported on an implant with a partially flat abutment shoulder.

In FIG. 5B, a cross-section of a one piece implant 500 having a planar platform 522 is shown. The planar surface enables the apical end of the prosthesis 600 to be thicker, thus increasing its strength.

When designing a dental abutment a compromise must be struck between the width of the abutment post and the width of the abutment shoulder. The abutment post provides strength and support to the prosthesis, as well as a retention surface in cases when the prosthesis is cemented to the abutment. Therefore a large width, and hence volume and surface area, is advantageous. A wide shoulder width, or chamfer depth on the other hand is also beneficial for the reasons outlined above.

The present invention provides a means of balancing these two conflicting requirements, by enabling areas of the planar platform to be increased while maintaining a large volume of abutment post.

Figure 6:
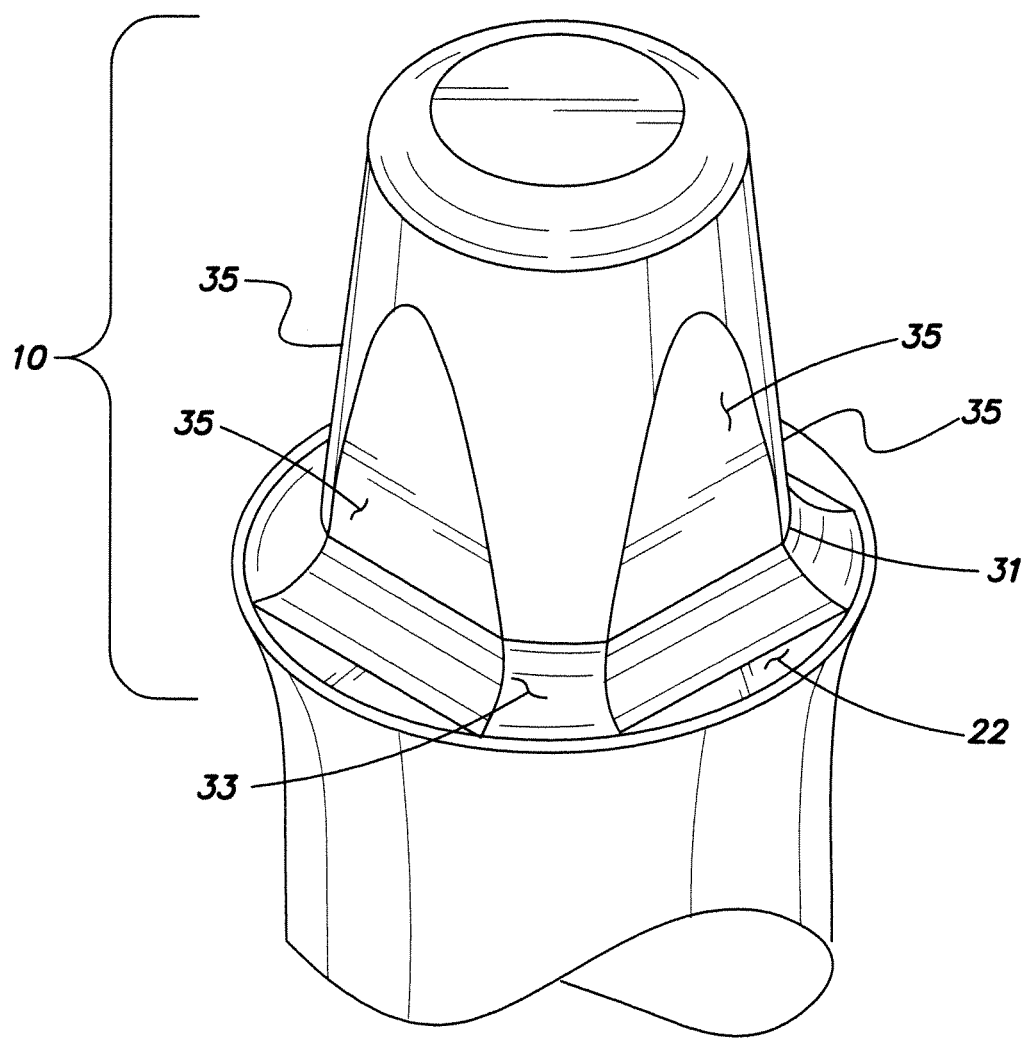
FIG. 6 shows a perspective view of a dental implant with an abutment according to the invention having four flat surfaces.

FIG. 6 shows a further embodiment of the present invention, in which four flat surfaces 35, again bevel surfaces, are provided. Each flat surface 35 extends to the base 31 of the post 30 and therefore forms a linear edge from which the chamfered surface 33 begins. The non-uniform chamfer surface 33 therefore contains eight angles. The additional flat surfaces 35 also increase the surface area of the planar platform 22. The chamfered surface 33 provides a direct, smooth transition between the flat surfaces 35, and other areas of the base 31, and the planar platform 22.

Figure 7:
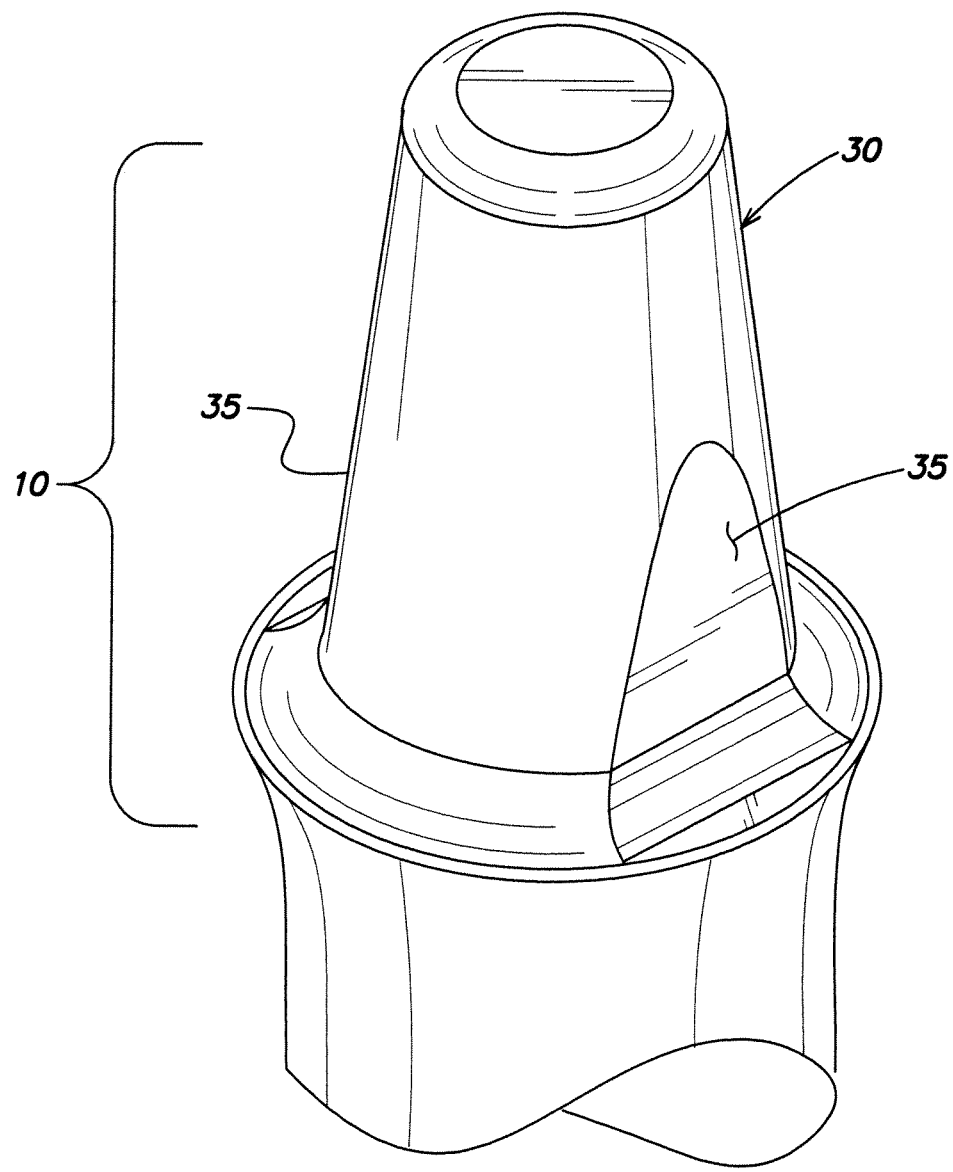
FIG. 7 shows a perspective view of another embodiment of a dental implant with an abutment according to the invention having two flat surfaces.
Figure 8:
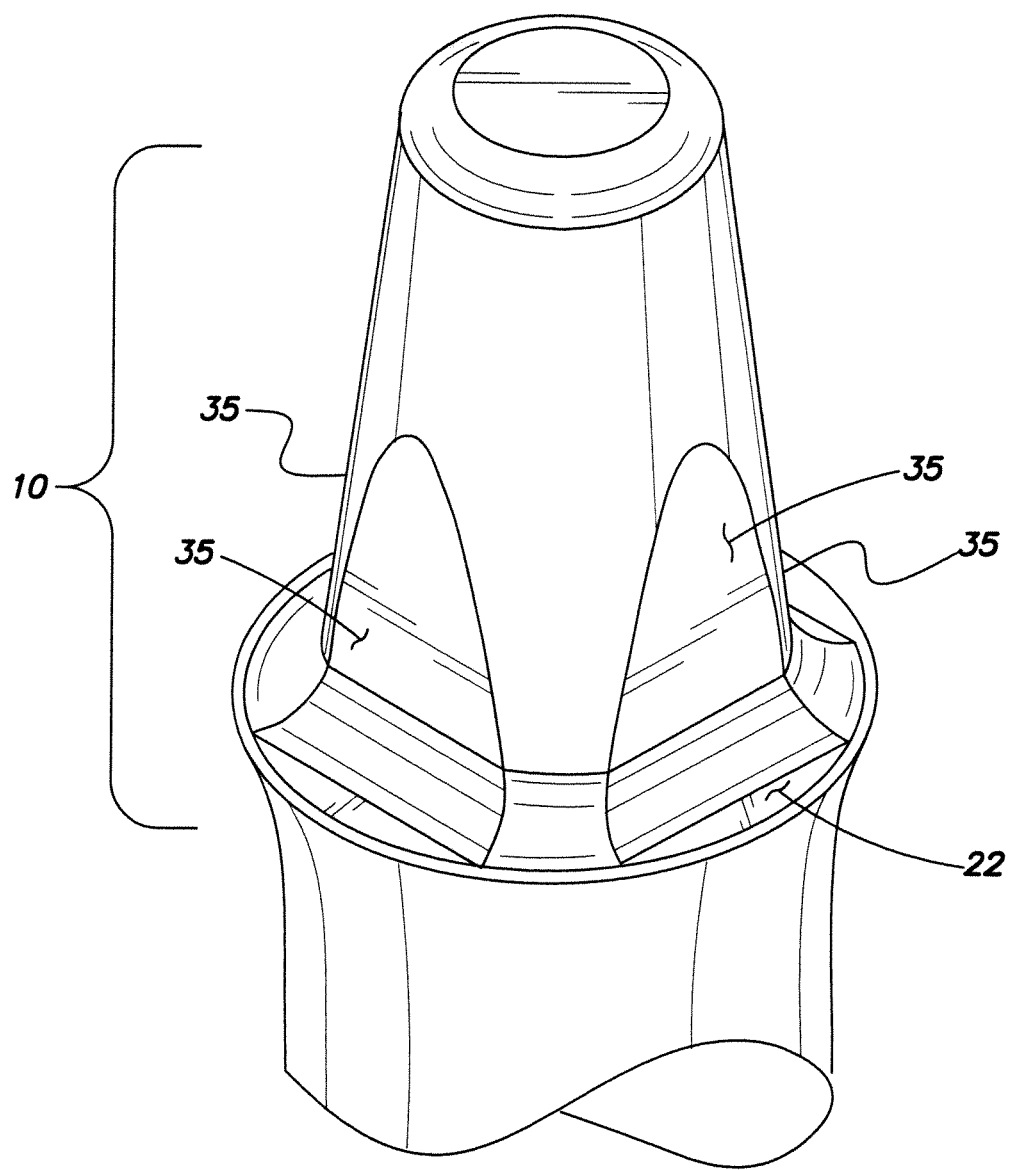
FIG. 8 shows a perspective view of another embodiment of a dental implant with an abutment according to the invention having four flat surfaces.

FIGS. 7 and 8 show further alternative embodiments of the present invention. The implants shown in these figures can be a one or two part implants. In these embodiments the length of the abutment post 30 is greater than in previous embodiments, although the length of the flat surfaces 35 has not been similarly increased. The surface area of these flat surfaces 35 should be sufficient to enable good gripping of the abutment as well as torque transmission. This latter quality is of particular importance when the implant is a one piece implant as the flat surfaces 35 can be used to rotate the implant to screw this into the bone.

Figure 9:
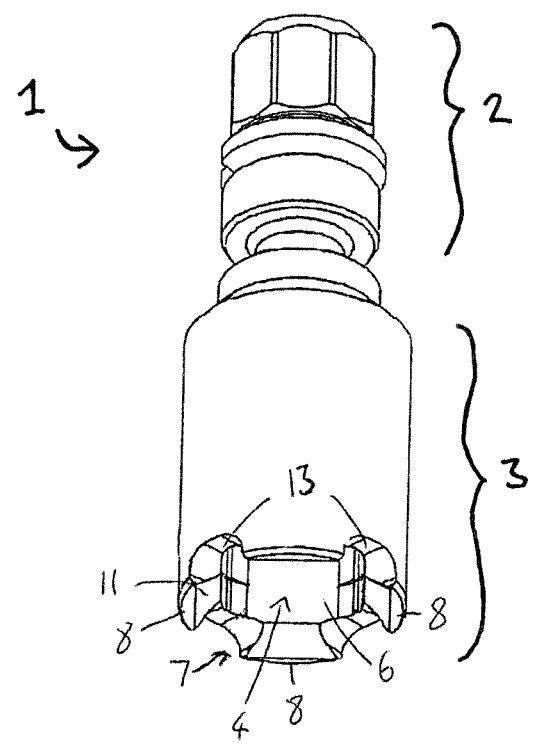
FIG. 9 shows a perspective view of an insertion tool for use with the abutment of FIG. 8.

Auxiliary pieces, such as those mentioned previously, can be shaped to match the post 30 in order to non-rotationally attach to the abutment. In addition, an insertion tool can be provided that enables torque to be transmitted to the abutment. An example of such an insertion tool is shown in FIG. 9.

Insertion tool 1 comprises a connecting part 2 for connection to a driving device, for example a dental handpiece or ratchet. Distal to this is an attachment part 3 for connecting to the abutment 10. Attachment part 3 comprises a cavity 4 for housing the abutment post 30. The inner walls of cavity 4 comprise flat surfaces 6 for engagement with the flat surfaces 35 of the abutment. At the distal end 7 of the insertion tool 1 abutment surfaces 8 are formed. These surfaces are shaped and positioned such that, when the insertion tool 1 is placed over the abutment and rotated such that flat surfaces 6 are aligned with flat surfaces 35, the abutment surfaces 8 engage the planar platform 32. In this embodiment, the abutment surfaces 8 only engage those parts of the platform 32 which are adjacent to the flat surfaces 35, and hence have a greater width. Cut outs 13 prevent any jamming between the cavity 4 and those parts of the chamfered surface 33 that start from the curved base 31 of the post 30. As these parts of the chamfer begin at a greater distance from the longitudinal axis, the chamfer extends further in the radial direction than those parts of the chamfer beginning at the flat surfaces 35. However in other embodiments the abutment surface may encircle the entire distal end 7 and thus contact the entire planar platform.

The planar platform 32 of the abutment 10 acts as a height stop, against which, when the insertion tool 1 is correctly seated, the abutment surfaces 8 abut. In this position maximum alignment is achieved between the flat surfaces 6 of the insertion tool 1 and those 35 of the abutment 10. Torque can thus be transmitted via these surfaces from the insertion tool to the abutment. Given the firm connection provided between the flat surfaces 6, 35 of the insertion tool 1 and the abutment 10, and the and abutment surfaces 8 and planar platform 32 it is not necessary for the insertion tool 1 to mirror the chamfered surface 33 of the abutment. Therefore a tapered transition 11 rather than a convex surface is provided between the abutment surfaces 8 and the flat surfaces 6.

Figure 10:
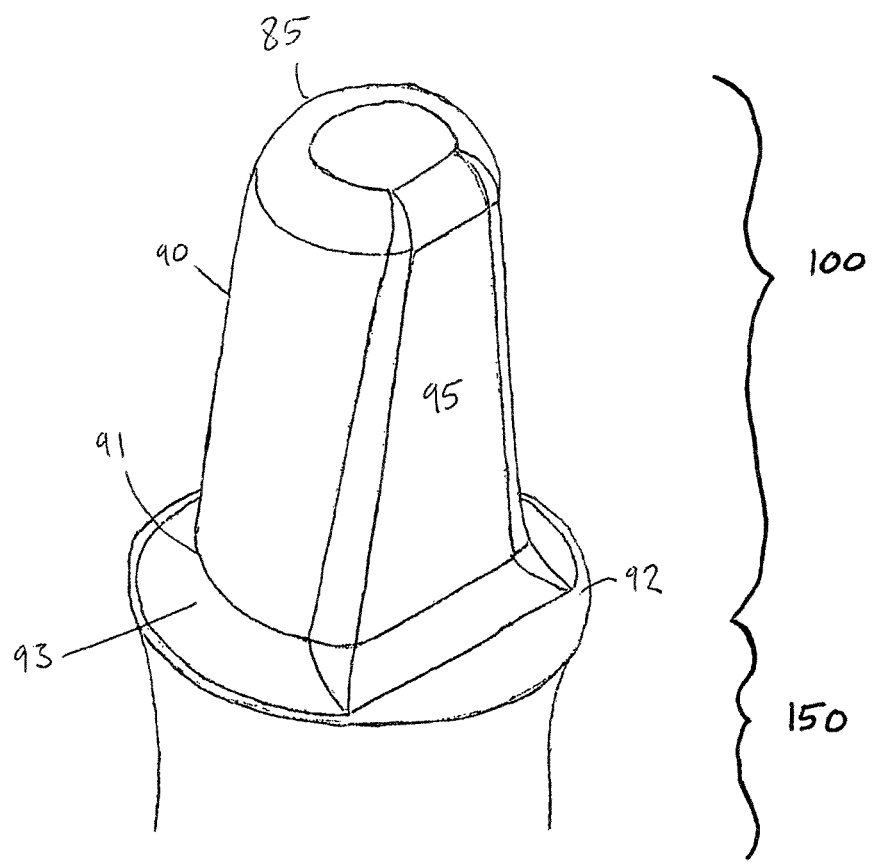
FIG. 10 shows a perspective view of an alternative embodiment of the abutment according to the present invention.

FIG. 10 shows an alternative embodiment of the present invention in perspective view. Here the abutment 100 forms an integral part of the anchoring part 150. The abutment 100 comprises a conical post 90 which is truncated and rounded at its coronal end 85. In this embodiment flat surface 95 is not a bevel surface but instead forms part of the non-circular geometric base of the conical post 90. The flat surface 95 therefore extends over the length of the abutment post 90. Chamfered surface 93 extends from the base 91 of the post 90. The chamfered surface 93 and planar platform 92 together form the abutment shoulder, on which in use the prosthesis rests. Chamfered surface 93 creates a smooth transition between the abutment post 90 and the planar platform 92. Due to the non uniform chamfer surface 93 the platform 92 has a greater surface area in the region of the flat surface 95, thus providing a more stable abutment base for the prosthesis and enabling the apical end of this prosthesis to be made thicker.

The above described embodiments are for illustrative purposes only and the skilled man will realize that many alternative arrangements are possible which fall within the scope of the claims. For example, the abutment post may be many alternative shapes, such as circular cylindrical or any other shape in which curved surfaces separate the flat surfaces. The flat surfaces may extend the full length of the post regardless of whether these surfaces are bevelled or otherwise produced. The abutment shoulder does not need to have a circular perimeter and can be, for example, wave-shaped and located remote from the anchoring part.

Viewed from one aspect the present invention comprises an abutment for a dental implant, which abutment has substantially the shape of a truncated cone, said abutment having a shoulder, and said truncated cone forming an outer surface, wherein the outer surface comprises an at least partially flat surface, which runs out in the shoulder.

Preferably the at least partially flat surface is arranged parallel to a longitudinal axis of the abutment.

Preferably the outer surface of the abutment comprises at least two at least partially flat surfaces.

Preferably the at least partially flat surfaces are arranged at an angle α, preferably of 90°, about a longitudinal axis of the abutment.

Preferably the at least partially flat surfaces are arranged lying opposite each other in pairs.

Preferably the outer surface of the abutment comprises four at least partially flat surfaces.

Preferably the abutment is formed in one piece with an anchoring part.

Preferably the abutment is made of a ceramic material.

Preferably the ceramic material is chosen from the group of zirconium oxide and aluminum oxide.

Preferably the ceramic material is a stabilized zirconium oxide containing 92.1 to 93.5% by weight of $ZrO_2$, 4.5 to 5.5% by weight of $Y_2O_3$, and 1.8 to 2.2% by weight of $HfO_2$.

Preferably the cone angle is in a range from 1° to 20°, preferably in a range from 4° to 10°.

Preferably the cone angle is substantially 6°.

Preferably the cone angle is substantially 8°.

According to another aspect the present invention comprises a dental implant comprising the abutment as laid out above.

The invention claimed is:

1. An abutment for supporting a dental prosthesis comprising:
   a post having a base, and
   a shoulder, wherein the shoulder comprises a concavely curved chamfer surface extending radially outwards from the base of the post and shoulder has a circular outer circumference,
   the post comprising at least one flat surface which runs directly into the chamfered surface such that the chamfered surface is non-uniform; and
   wherein the shoulder further comprises a planar platform, the curved chamfer surface providing a smooth transition between the base of the post and the planar platform and wherein said planar platform extends around the full circumference of the abutment shoulder and is wider in a region adjacent to the at least one flat surface.

2. An abutment as claimed in claim 1, wherein the post has a fully or partially circular geometric base such that the at least one flat surface is interposed between curved surfaces.

3. The abutment as claimed in claim 1, wherein the at least one flat surface is arranged parallel to a longitudinal axis of the post.

4. The abutment as claimed in claim 1, wherein the at least one flat surface is a bevel surface.

5. The abutment as claimed in claim 1, wherein the abutment comprises at least two flat surfaces.

6. The abutment as claimed in claim 5, wherein the at least two flat surfaces are arranged at an angle α relative to each other about a longitudinal axis of the abutment.

7. The abutment as claimed in claim 6, wherein the angle is 90°.

8. The abutment as claimed in claim 1, wherein the post has the general shape of a truncated cone.

9. The abutment as claimed in claim 1, wherein the abutment is formed of a ceramic material.

10. The abutment as claimed in claim 1, wherein the abutment is formed in one piece with an anchoring part.

11. The abutment as claim 1n claim 1, wherein the abutment further comprises a connection section apical to the shoulder which is configured for connection to a dental implant.

12. A dental implant comprising an anchoring portion for anchoring in bone and, integrally formed with said anchoring portion, an abutment as claimed in claim 1.

* * * * *